United States Patent
Al Marzouqi et al.

(10) Patent No.: US 11,609,174 B2
(45) Date of Patent: Mar. 21, 2023

(54) METHOD AND SYSTEM FOR DETERMINING PERMEABILITY OF A POROUS MEDIUM

(71) Applicant: Khalifa University of Science and Technology, Abu Dhabi (AE)

(72) Inventors: Hasan Al Marzouqi, Abu Dhabi (AE); Sandra Vega, Abu Dhabi (AE); Huafeng Sun, Abu Dhabi (AE)

(73) Assignee: KHALIFA UNIVERSITY OF SCIENCE AND TECHNOLOGY, Abu Dhabi (AE)

( * ) Notice: Subject to any disclaimer, the term of this patent is extended or adjusted under 35 U.S.C. 154(b) by 65 days.

(21) Appl. No.: 16/761,777

(22) PCT Filed: Nov. 6, 2017

(86) PCT No.: PCT/IB2017/056918
§ 371 (c)(1),
(2) Date: May 5, 2020

(87) PCT Pub. No.: WO2019/086938
PCT Pub. Date: May 9, 2019

(65) Prior Publication Data
US 2020/0333234 A1   Oct. 22, 2020

(51) Int. Cl.
*G01N 15/08* (2006.01)
*G01N 23/04* (2018.01)
(Continued)

(52) U.S. Cl.
CPC .......... *G01N 15/08* (2013.01); *G01N 23/046* (2013.01); *G01N 33/24* (2013.01); *G06T 7/11* (2017.01);
(Continued)

(58) Field of Classification Search
CPC ........ G01N 15/00; G01N 15/08; G01N 23/00; G01N 23/04; G01N 23/046; G01N 33/24;
(Continued)

(56) References Cited

U.S. PATENT DOCUMENTS

| 4,982,086 A | * | 1/1991 | Withjack | G01N 33/24 |
| | | | | 250/258 |
| 5,297,420 A | * | 3/1994 | Gilliland | G01N 33/241 |
| | | | | 73/38 |

(Continued)

FOREIGN PATENT DOCUMENTS

| BR | 112013015288 B1 * | 9/2021 | ........... G01V 99/005 |
| CN | 104237103 A | 12/2014 | |

(Continued)

OTHER PUBLICATIONS

ISSN 2202-0586 "Estimated porosity from CT scans of high permeability core plugs"—Feb. 26, 2019.*

(Continued)

*Primary Examiner* — Nguyen Q. Ha
(74) *Attorney, Agent, or Firm* — Dennemeyer & Associates LLC

(57) ABSTRACT

A method for determining permeability of a porous medium is described which comprises the steps: a) obtaining a three-dimensional picture of the porous medium by an imaging system, b) dividing the three-dimensional picture into a number n of two-dimensional parallel slices, wherein n is an integer of 2 or more, c) identifying one or more pores in a first outermost slice ($n_1$) using a grid which defines image pixels, d) identifying one or more pores in a second slice ($n_2$) directly neighboring the first outermost slice ($n_1$) using the same grid which defines image pixels as for the first outermost slice ($n_1$), and e) labelling the one or more pores in the second slice ($n_2$) as connected if at least one of its neighbours in the first outermost slice ($n_1$) is a pore to (Continued)

give a number of connected pores as a connectivity result. Also described is a system comprising means for carrying out such a method.

10 Claims, 1 Drawing Sheet

(51) Int. Cl.
 *G01N 33/24* (2006.01)
 *G06T 7/11* (2017.01)
 *G01N 23/046* (2018.01)
(52) U.S. Cl.
 CPC .............. *G01N 2015/0846* (2013.01); *G06T 2207/10081* (2013.01)
(58) Field of Classification Search
 CPC . G01N 2015/0846; G01N 2207/10081; G06K 9/00; G06T 7/11
 See application file for complete search history.

(56) References Cited

U.S. PATENT DOCUMENTS

| | | | |
|---|---|---|---|
| 6,516,080 B1 | 2/2003 | Nur | |
| 9,348,056 B2 * | 5/2016 | Fredrich | ................... G01V 8/00 |
| 2010/0135536 A1 | 6/2010 | Dvorkin et al. | |
| 2013/0262028 A1 * | 10/2013 | De Prisco | .............. G01N 33/24 |
| | | | 702/156 |
| 2013/0308831 A1 * | 11/2013 | Dvorkin | ................ G06T 7/0004 |
| | | | 382/109 |
| 2014/0019054 A1 * | 1/2014 | De Prisco | .............. G01N 15/08 |
| | | | 702/12 |

FOREIGN PATENT DOCUMENTS

| | | | | |
|---|---|---|---|---|
| CN | 105487121 A | 4/2016 | | |
| WO | 0123829 A2 | 4/2001 | | |
| WO | WO-2011149808 A3 * | 4/2012 | ............. | G01N 33/24 |
| WO | 2016/007170 A1 | 1/2016 | | |
| WO | 2016115471 A1 | 7/2016 | | |

OTHER PUBLICATIONS

International Search Report issued in connection with PCT Application No. PCT/IB2017/036918, dated Jan. 16, 2019.
Arns, C. M., Knackstedt, M., Pinczewski, M. and Garboczi, E., Computation of linear elastic properties from microtomographic images: methodology and agreement between theory and experiment, Geophysics, 2002, 67: 1396-1405.
Garboczi, E. and Day, A., Algorithm for computing the effective linear elastic properties of heterogeneous materials: Three dimensional results for composites with equal phase poisson ratios, Journal of the Mechanics and Physics of Solids, 1995, 43: 1349-1362.
Jouini, M. S. and Vega, S. 2010. Elastic properties computation and fluid substitution simulation from X-ray CT scan images in Middle East carbonates sample, Eos Trans, AGU 91(49), American Geophysical Union, Dec. 2010, San Francisco, California, USA.
Jouini, M. S. and Vega S, Numerical simulations of linear elastic properties of carbonates rock samples using 3D computed tomography images in EAGE GeoInformatic Theoretical and Applied Aspects Conference, Kyiv, Ukraine, 2011.
Jouini, M. S. and Vega S., Simulation of elastic properties in carbonates, The Leading Edge Journal, 30 (12): 838-842, 2011.
Jouini, M. S. and Vega, S. 2012. Simulation of carbonate rocks elastic properties using 3D XRay computed tomography images based on Discrete Element Method and Finite Element Method, in the 46th American Rock Mechanics Association conference, Chicago, USA, 2012.
Sun H F, Vega S, Tao G, Analysis of Heterogeneity and Permeability Anisotropy in Carbonate Rock Samples Using Digital Rock Physics. Journal of Petroleum Science and Engineering, 2017, 156: 419-429.
Sun H F, Tao G, Vega S, Al-Suwaidi A. Simulation of Gas Flow in Organic-Rich Mudrocks Using Digital Rock Physics. Journal of Natural Gas Science and Engineering, 2017, 41: 17-29.
Sun H F, Tao G, Vega S, Wang B, Liu H, Li, K S. Multi-Scale CT Image Analysis of Digital Carbonate Rock. Paper presented at the 79th EAGE Conference & Exhibition, Paris, France, Jun. 12-Jun. 15, 2017.
Li K S, Gao J, Wu C, Zhao X, Chen F G, Liu S, and Sun H. The New Tool Design of Ultra-deep Azimuthal Electromagnetic Resistivity Logging-While-Drilling based on Gray Relational Analysis Method. Paper presented at the 79th EAGE Conference & Exhibition, Paris, France, Jun. 12-Jun. 15, 2017.
Sun H F, Vega S, Tao G, Yong H, Li B. Estimation of Petrophysical Parameters of a Heterogeneous Carbonate Rock Sample with Multiscale CT Images E-Poster in 2016 PIRC R&D Conference and Exhibition, Nov. 21, 2016.
Sun H F, Vega S, Tao G. Determination of Transport Properties in Carbonate Rock Sample Using Multi-scale CT Images. Paper presented at the 78th EAGE Conference & Exhibition, Reed Messe Wien, Vienna, Austria, May 30-Jun. 2, 2016.
Li K S, Gao J, Li H, Sun H F. Porosity Calculation of Horizontal Wells when Acoustic Slowness Is Abnormal—A Case Study in Northern Ordos Basin, China. Paper presented at the 78th EAGE Conference & Exhibition, Reed Messe Nien, Vienna, Austria, May 30-Jun. 2, 2016.
Sun H F, Vega, S, Tao G. Study of Heterogeneity in Carbonate Rock Samples Using Digital Rock Physics. Paper Presented at the 3rd EAGE Workshop on Rock Physics, Istanbul, Turkey, Aug. 15-18, 2015.
Sun H F, Vega S, Tao G. Simulation of Shale Gas Flow in Nano Pores with Parallel Lattice Boltzmann Method. Paper presented at the 77th EAGE Conference & Exhibition, IFEMA Madrid, Spain, Jun. 1-4, 2015.
Chen P, Tao G, Dong M J, Sun H F. The Effects of The Pore Throat Roughness on the Water-Oil Flow in Rock Reservoirs. Progress in Geophysics, 2013, 28(2):0824-0829.
Li Y, Xiao L Z, Sun H F. Analyses of Influencing Factors of Hydrocarbon Identification Using NMR Time Domain Analysis. Chinese Journal of Magnetic Resonance, 2012, 29(1): 21-31.
Di D J, Tao G, Sun H F, Yue W Z. Analysis and Consideration of Formation Testing While Drilling Technology. Well Logging Technology, 2012, 36(3): 294-299.
Sun H F, Tao G, Zhou Y M, etc. The Evaluative Roles of WFT in Formation and Reservoir Evaluations. Well Logging Technology, 2010, 34(4): 314-322.
Saenger, E.H., Vialle S., Lebedev, M., Uribe, D., Osorno, M., Duda, M., and Steeb, H. 2016, Digital carbonate rock physics. Solid Earth Discuss, 7(4):1185-1197.
Saenger, E.H., Enzmann, F., Keehm, Y., and Steeb, H. 2011. Digital rock physics: Effect of fluid viscosity on effective elastic properties Journal of Applied Geophysics, 74, 236-241.
Bultreys, T., Boever, W.D., Hoorebeke, L. V., Cnudde, V. 2015. A multi-scale, image-based pore network modeling approach to simulate two-phase flow in heterogeneous rock. Paper presented at the International Symposium of the Society of Core Analysist held in St. John's Newfoundland and Labrador, Canada, Aug. 16-21, 2015.
Teles, A.P., Machado, A.C., Pepin, A., Bize-Forest, N., Lopes, R.T., Lima, I. 2016. Analysis of subterranean Pre-salt carbonate reservoir by X-ray computed microtomography. Journal of Petroleum Science and Engineering, 144: 113-120.
Office Action in Brazilian application No. BR112020009026-3 dated Sep. 9, 2022.

* cited by examiner

|   |   |   |
|---|---|---|
| 0 | 0 | 0 |
| 0 | 1 | 0 |
| 0 | 0 | 0 |

(a)

|   |   |   |
|---|---|---|
| 1 | 1 | 1 |
| 1 | 1 | 1 |
| 1 | 1 | 1 |

|   |   |   |
|---|---|---|
| 1 | 0 | 0 |
| 0 | 0 | 0 |
| 0 | 0 | 0 |

(a)

|   |   |   |
|---|---|---|
| 1 | 1 | 1 |
| 1 | 1 | 1 |
| 1 | 1 | 1 |

METHOD AND SYSTEM FOR DETERMINING PERMEABILITY OF A POROUS MEDIUM

CROSS-REFERENCE TO RELATED APPLICATIONS

This is a 35 U.S.C. 371 National Stage Patent Application of International Application No. PCT/IB2017/056918, filed Nov. 6, 2017, which is hereby incorporated by reference in its entirety.

The present invention is directed to a method for determining permeability of a porous medium, especially a method using a combination of image translation and logical operations. The present invention is furthermore directed to a system for determining permeability of a porous medium, i.e. a system which is capable of carrying out a method for determining permeability of a porous medium.

BACKGROUND

Digital Rock Physics (DRP) has been developed and commercialized rapidly in the last few years. Digital Rock Physics is a relative new technology that is able to compute rock properties from digital rock images. Some relevant publications are listed hereinafter:

Arns, C. M., Knackstedt, M., Pinczewski, M. and Garboczi, E. 2002. Computation of linear elastic properties from microtomographic images: methodology and agreement between theory and experiment. Geophysics. 67: 1396-1405.

Garboczi, E. and Day, A. 1995. Algorithm for computing the effective linear elastic properties of heterogeneous materials: Three dimensional results for composites with equal phase poison ratios. Journal of the Mechanics and Physics of Solids. 43: 1349-1362.

Jouini, M. S. and Vega, S. 2010. Elastic properties computation and fluid substitution simulation from X-ray CT scan images in Middle East carbonates sample. Eos Trans. AGU. 91(49). American Geophysical Union, December 2010, San Francisco, Calif., USA.

Jouini, M. S. and Vega S. 2011a. Numerical simulations of linear elastic properties of carbonates rock samples using 3D computed tomography images. in EAGE GeoInformatic. Theoretical and Applied Aspects Conference, Kyiv, Ukraine, 2011.

Jouini, M. S. and Vega S. 2011b. Simulation of elastic properties in carbonates. The Leading Edge Journal, 30 (12): 838-842, 2011.

Jouini, M. S. and Vega, S. 2012. Simulation of carbonate rocks elastic properties using 3D X-Ray computed tomography images based on Discrete Element Method and Finite Element Method. in the 46th American Rock Mechanics Association conference, Chicago, USA, 2012.

Nur A. M. 2003. Numerical method of estimating physical properties of three dimensional porous media. U.S. Pat. No. 6,516,080 B1.

The technology of Digital Rock Physics has the advantage that it is non-destructive and enables to do computational experiments in shorter time than in the lab. However, this technique is not faultless; it counts with some limitations and needs to be better developed. Oil companies in the world are using more and more this technique as an alternative, due to its cleanness and relative fast results. Its major use is for calculating porosity and permeability, and more recently for elastic properties and capillarity pressure curves.

In-house codes can help to count with open algorithms adapted for e.g. local rocks. However, absolute permeability codes can be in general computational costly and time consuming compared with experiments in the lab. Therefore, finding optimized codes that reduce the computer and time requirements are highly needed. The present invention approaches specifically the optimization of permeability codes in DRP, reducing computational time and memory.

Lattice-Boltzmann (LBM) method is one of the methods that are frequently used to estimate permeability from CT scans of rock samples. LBM simulates fluid flow based on the principles of molecular dynamics and statistical mechanics (see e.g. Ju, Y., Wang, J., and Gao, F. 2014. Lattice-Boltzmann Simulation of Microscale CH4 Flow in Porous Rock Subject to Force-induced Deformation. China Science Bull, 59(26): 3292-3303; and Kang Q, Lichtner P C, Zhang D. 2006. Lattice Boltzmann pore-scale model for multicomponent reactive transport in porous media. J Geophys Res 111:B05203).

The Finite Difference method (FDM) is another method for fluid simulation that can be used permeability estimation (see e.g. Oren P E, Bakke S. 2002. Process based reconstruction of sandstones prediction of transport properties. Transp Porous Media 46:311-343 and Mostaghimi, P., Blunt, M. J., and Bijeljic, B. 2012. Computations of absolute permeability on micro-CT images: Mathematical Geosciences, vol. 45, no. 1, pp. 103-125).

These methods are computationally intensive. For example, about five hours are needed to get the results when using LBM to do the simulation on digital rock model with image size of 200×200×200 with a modern PC. In addition, these algorithms demand high memory requirements and image with large sizes will not run on typical PC's.

SUMMARY OF THE INVENTION

It is an object of the present invention to provide a method and a system for determining permeability of a porous medium, especially permeability of a rock, which gives a reliable estimate for permeability with significant reductions in computational time.

It is a further object of the present invention to provide a method and a system for determining permeability of a porous medium, especially permeability of a rock, which requires only limited memory, which can process images of small sizes and which runs on typical PC's.

In order to achieve one or more of the mentioned objects, the present invention provides a method for determining permeability of a porous medium, comprising the steps:
a) obtaining a three-dimensional picture of the porous medium by an imaging system,
b) dividing the three-dimensional picture into a number n of two-dimensional parallel slices, wherein n is an integer of 2 or more,
c) identifying one or more pores in a first outermost slice ($n_1$) using a grid which defines image pixels,
d) identifying one or more pores in a second slice ($n_2$) directly neighboring the first outermost slice ($n_1$) by using the same grid which defines image pixels as for the first outermost slice ($n_1$),
e) labelling the one or more pores in the second slice ($n_2$) as connected if at least one of its neighbours in the first outermost slice ($n_1$) is a pore to give a number of connected pores as a connectivity result.

It is preferred that in the method of the present invention steps c) to e) are a first iteration and that these steps are iterated to subsequent slices ($n_3$, $n_4$, ... ) until a last slice ($n_{last}$) is reached, wherein in each iteration the connectivity result in the previous iteration is regarded as a first slice, to give a number of connected pores as a final connectivity result.

It is also preferred in the present invention that the inventive method is repeated with respect to steps c) to e) in the opposite direction, i.e. starting from the last slice ($n_2$ or $n_{last}$), wherein after the repetition an average number of connected pores is computed as an average connectivity result. More preferably, a permeability connectivity index (PCI) is thereafter computed which is defined as the average number of connected pores divided by the total number of image pixels.

It is furthermore preferred that in the method of the present invention the grid defines squared image pixel, wherein each image pixel has particularly preferable nine neighbouring image pixels in the previous and/or the subsequent slice.

In a specifically preferred embodiment according to the present invention the porous medium is a rock.

In order to achieve one or more of the mentioned objects, the present invention furthermore provides a system comprising means for carrying out the method of the present invention as described herein. Preferably, the means comprise an imaging system and a computer. It is also preferable that the means comprise an imaging system which is a computed tomography scanner, especially preferably in combination with a further computer.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

BRIEF DESCRIPTION OF THE DRAWINGS

The present invention will be described with reference to the accompanying drawings of which:

FIG. 1 is an example used to illustrate the operation of the developed pore connectivity index; (a) first slice, e.g. $n_1$, (b) second slice, e.g. $n_2$. Pores are labelled by the index 1.

FIG. 2 is another example used to illustrate the operation of the developed pore connectivity index; (a) first slice, e.g. $n_1$, (b) second slice, e.g. $n_2$. Pores are labelled by the index 1.

DETAILED DESCRIPTION OF THE INVENTION

According to the present invention, there is provided a method for determining permeability of a porous medium, comprising the steps:
a) obtaining a three-dimensional picture of the porous medium by an imaging system,
b) dividing the three-dimensional picture into a number n of two-dimensional parallel slices, wherein n is an integer of 2 or more,
c) identifying one or more pores in a first outermost slice ($n_1$) using a grid which defines image pixels,
d) identifying one or more pores in a second slice ($n_2$) directly neighboring the first outermost slice ($n_1$) while using the same grid which defines image pixels as used for the first outermost slice ($n_1$),
e) labelling the one or more pores in the second slice ($n_2$) as connected if at least one of its neighbours in the first outermost slice ($n_1$) is a pore to give a number of connected pores as a connectivity result.

In the inventive method, the image is preferably an electronical image so that it can be easily processed by e.g. a computer. Further, the two-dimensional parallel slices of the produced image are indexed as $n_1$ and $n_2$ for the first two slices. In case three slices are obtained in step b), the slices would be indexed as $n_1$, $n_2$ and $n_3$. The same logic applies in case n is an integer of 4 or more. The final or last slice of a set of slices as produced in step b) is indexed as $n_{last}$. So in case in total e.g. 100 slices are created, $n_{last}$ would equal $n_{100}$. The entire stack of slices form the three-dimensional picture obtained in step a), and its outermost layers are slices $n_1$ and $n_{last}$. Further, in the sense of this invention slice $n_1$ has one direct neighbor, namely slice $n_2$, while slice $n_2$ itself typically has two direct neighbours, namely slices $n_1$ and $n_3$—provided $n_3$ exists; otherwise $n_2$ is equal to $n_{last}$ and thus also has only one direct neighbour, namely $n_1$. The slices $n_1$ and $n_{last}$ are the outermost slices of the stack of n slices generated in step b).

It is preferable according to the present invention that in the inventive method steps c) to e) are seen as a first iteration. By step e) this iteration gives a connectivity result. In a subsequent step and provided n is larger than 2 this first connectivity result is used a first slice and steps c) to e) are reiterated using this newly generated first slice and the subsequent slice. For example, in case the image is broken up into three slices and after having carried out steps a) to e) for the first time, the result for slices $n_1$ and $n_2$ is used as a new first slice, which could be labelled e.g. $n_{1'}$. This new first slice $n_{1'}$ is then used in a repeated step c) and e) and slice $n_3$ is used in repeated step d) and e). So after having carried out the inventive method once, steps c) to e) are preferably iterated to subsequent slices ($n_3$, $n_4$, . . . ) depending on the number of slices until the last slice ($n_{last}$) is reached. This means that in each iteration the connectivity result of the previous iteration is regarded as a first slice, to give a number of connected pores as a final connectivity result.

Following the afore-said protocol pores penetrating through the imaged porous medium basically perpendicular to the plane of the generated parallel and two-dimensional images can be identified. It is preferable for an enhanced accuracy of the measurement to redo the entire exercise, this time reversing the order of the slices, i.e. using $n_{last}$ as the first slice and using $n_1$ as the last slice. Thereafter, the resulting connectivities can be averaged. It is therefore particularly preferable in this invention that the method is repeated with respect to steps c) to e) in the opposite direction, i.e. starting from the last slice ($n_2$ or $n_{last}$), wherein after the repetition an average number of connected pores is computed as an average connectivity result.

It is furthermore preferable according to the present invention to calculate a permeability connectivity index (PCI) to obtain a measure for the permeability of the analyzed porous medium. Accordingly, it is preferable that in the inventive method a permeability connectivity index (PCI) is computed which is defined as the average number of connected pores divided by the total number of image pixels.

In a simple, analytically complete and hence particularly preferable method according to the present invention the grid defines squared image pixels, i.e. two-dimensional rectangular pixels of equal length and width are defined by the grid. While other shapes such as hexagons are also contemplated the computing done with image pixels having the shape of a square is more efficient in reducing computational time and memory. In this case the image pixels are preferably arranged such that each image pixel has nine neighbouring image pixels in the previous and/or the subsequent slice.

When the porous medium analyzed by the method of the present invention is actually a rock, the present method is particularly useful for the oil and gas industry.

In order to achieve one or more of the mentioned objects, the present invention furthermore provides a system comprising means for carrying out the method of the present invention as described herein. Preferably, the means comprise an imaging system and a computer. It is also preferable that the means comprise an imaging system which is a computed tomography scanner, especially preferably in combination with a further computer.

A particularly preferred embodiment of the invention is now described. According to this particularly preferred embodiment of the invention, the inventive method is a method for determining the permeability of a rock using a combination of image translation and logical operations. In this particular embodiment the developed method depends on tracking the connectivity of pores within a rock sample. The method first assumes that pores in the first slice are filled with fluids. Next it finds the pores filled with fluids in the second slice. A pore in the second sliced is labelled to be filled with fluid if it is connected to a pore in the first slice. A pore is labelled connected if one of its nine neighbours in the previous slice are pores. FIG. 1 and FIG. 2 show examples that illustrate the connectivity between two slices. These figures show two slices of an image of size 3 by 3.

In FIG. 1 only the centre pixel in the first slice is a pore. In the second slice, all pixels indicate the presence of pores. According to the connectivity definition as used in the present invention all the pores in the second image are connected to the first slice and will allow fluid to pass through them. If the first image did not contain pores then no pores in the second slice would be labelled connected.

In the second example, shown in FIG. 2, only the upper left corner element of the first slice is labelled as a pore. The output of the corresponding method step will indicate the presence of 4 connected pores in the upper left corner of the image. The remaining pores are not connected.

The preceding connectivity computation is iterated to subsequent slices. In each iteration, the connectivity result in the previous iteration is regarded as a first slice. Once the last slice is reached the number of connected pores is used as a measure for the permeability of the rock sample. To reach a more reliable estimate the previous operation is repeated in the opposite direction (i.e. starting from the last slice).

Finally, a permeability connectivity index (PCI) is computed which is defined as the average of the number of connected pores found in the two computed directions divided by the total number of image pixels.

The experiments underlying the present invention established a linear relationship between PCI values and rock permeability index. Computing PCI values for a sample of rocks with varying permeability values is preferable as a pre-processing step to get the parameters calibrating the relationship between PCI and rock permeability index. This calibration process allows to address variations between different scanners and the use of different imaging resolutions. The invention therefore preferably includes a calibration step to be performed on e.g. a computed tomography (CT) scanner from which data is acquired.

Computation of pore connectivity between slices can be performed using binary logical operations. The simplicity of the proposed method and the use of binary logical operations make the developed permeability index an attractive alternative to other methods frequently used in practice.

The invention delivers a reliable estimate for rock permeability computation with significant reductions in computational time.

Although an illustrative embodiment of the invention has been shown and described, it is to be understood that various modifications and substitutions may be made by those skilled in the art without departing from the novel spirit and scope of the invention.

FURTHER REFERENCES

Journal
  Sun H F, Vega S, Tao G. Analysis of Heterogeneity and Permeability Anisotropy in Carbonate Rock Samples Using Digital Rock Physics. *Journal of Petroleum Science and Engineering*, 2017, 156: 419-429. (IF 1.873)
  Sun H F, Tao G, Vega S, Al-Suwaidi A. Simulation of Gas Flow in Organic-Rich Mudrocks Using Digital Rock Physics. *Journal of Natural Gas Science and Engineering*, 2017, 41: 17-29. (IF 2.718)
Conference
  Sun H F, Tao G, Vega S, Wang B, Liu H, Li, K S. Multi-Scale CT Image Analysis of Digital Carbonate Rock. Paper presented at the $79^{th}$ EAGE Conference & Exhibition, Paris, France, 12 June-15 Jun. 2017.
  Li K S, Gao J, Wu C, Zhao X, Chen F G, Liu S, and Sun H. The New Tool Design of Ultra-deep Azimuthal Electromagnetic Resistivity Logging-While-Drilling based on Gray Relational Analysis Method. Paper presented at the $79^{th}$ EAGE Conference & Exhibition, Paris, France, 12 June-15 Jun. 2017.
  Sun H F, Vega S, Tao G, Yong H, Li B. Estimation of Petrophysical Parameters of a Heterogeneous Carbonate Rock Sample with Multi-scale CT Images. E-Poster in 2016 PIRC R&D Conference and Exhibition, Nov. 21, 2016.
  Sun H F, Vega S, Tao G, Yong H, Li B. Estimation of Petrophysical Parameters of Heterogeneous Carbonate Rock Sample with Multi-Scale CT Images. SPE-183114-MS. Paper presented at Abu Dhabi International Petroleum Exhibition and Conference, 7-10 November, Abu Dhabi, U A E, 2016.
  Sun H F, Vega S, Tao G. Determination of Transport Properties in Carbonate Rock Sample Using Multi-scale CT Images. Paper presented at the 78th EAGE Conference & Exhibition, Reed Messe Wien, Vienna, Austria, 30 May-2 Jun. 2016.
  Li K S, Gao J, Li H, Sun H F. Porosity Calculation of Horizontal Wells when Acoustic Slowness Is Abnormal—A Case Study in Northern Ordos Basin, China. Paper presented at the 78th EAGE Conference & Exhibition, Reed Messe Wien, Vienna, Austria, 30 May-2 Jun. 2016.

Sun H F, Tao G, Vega S. Study on Permeability Anisotropy in Carbonate Reservoir Samples Using Digital Rock Physics. SPE-177540-MS. Paper Presented at Abu Dhabi International Petroleum Exhibition and Conference, 9-12 November, Abu Dhabi, U A E, 2015.

Sun H F, Vega, S, Tao G. Study of Heterogeneity in Carbonate Rock Samples Using Digital Rock Physics. Paper Presented at the 3rd EAGE Workshop on Rock Physics, Istanbul, Turkey, 15-18 Aug. 2015.

Sun H F, Vega S, Tao G. Simulation of Shale Gas Flow in Nano Pores with Parallel Lattice Boltzmann Method. Paper presented at the 77th EAGE Conference & Exhibition, IFEMA Madrid, Spain, 1-4 Jun. 2015.

Chen P, Tao G, Dong M J, Sun H F. The Effects of The Pore Throat Roughness on the Water-Oil Flow in Rock Reservoirs. *Progress in Geophysics,* 2013, 28(2):0824-0829.(in Chinese)

Li Y, Xiao L Z, Sun H F. Analyses of Influencing Factors of Hydrocarbon Identification Using NMR Time Domain Analysis. *Chinese Journal of Magnetic Resonance,* 2012, 29(1): 21-31. (in Chinese)

Di D J, Tao G, Sun H F, Yue W Z. Analysis and Consideration of Formation Testing While Drilling Technology. *Well Logging Technology,* 2012, 36(3): 294-299. (in Chinese)

Sun H F, Tao G, Zhou Y M, etc. The Evaluative Roles of WFT in Formation and Reservoir Evaluations. *Well Logging Technology,* 2010, 34(4): 314-322. (in Chinese)

Others

Saenger, E. H., Vialle S., Lebedev, M., Uribe, D., Osorno, M., Duda, M., and Steeb, H. 2016. Digital carbonate rock physics. Solid Earth Discuss, 7(4):1185-1197.

Saenger, E. H., Enzmann, F., Keehm, Y., and Steeb, H. 2011. Digital rock physics: Effect of fluid viscosity on effective elastic properties. Journal of Applied Geophysics, 74, 236-241.

Bultreys, T., Boever, W. D., Hoorebeke, L. V., Cnudde, V. 2015. A multi-scale, image-based pore network modeling approach to simulate two-phase flow in heterogeneous rock. Paper presented at the International Symposium of the Society of Core Analysist held in St. John's Newfoundland and Labrador, Canada, 16-21 Aug. 2015.

Teles, A. P., Machado, A. C., Pepin, A., Bize-Forest, N., Lopes, R. T., Lima, I. 2016. Analysis of subterranean Pre-salt carbonate reservoir by X-ray computed microtomography. Journal of Petroleum Science and Engineering, 144: 113-120.

The invention claimed is:

1. A method for determining permeability of a porous medium, comprising the steps:
    a) obtaining a three-dimensional picture of the porous medium by an imaging system,
    b) dividing the three-dimensional picture into a number n of two-dimensional parallel slices, wherein n is an integer of 2 or more,
    c) identifying one or more pores in a first outermost slice ($n_1$) using a grid which defines image pixels of the outermost slice ($n_1$),
    d) identifying one or more pores in a second slice ($n_2$) directly neighboring the first outermost slice ($n_1$) using the same grid, which defines image pixels of the second slice ($n_2$), as for the first outermost slice ($n_1$),
    e) labelling the one or more pores in the second slice ($n_2$) as connected to the one or more pores in the first outermost slice ($n_1$) if the one or more pores in the second slice ($n_2$) neighbors the one or more pores in the first outermost slice ($n_1$) to give a number of connected pores as a connectivity result.

2. The method of claim 1 wherein steps c) to e) are a first iteration and wherein these steps are iterated to subsequent slices ($n_3, n_4, \ldots$) until a last slice ($n_{last}$) is reached, wherein in each iteration the connectivity result in the previous iteration is regarded as a first slice, to give a number of connected pores as a final connectivity result.

3. The method of claim 1, wherein the method is repeated with respect to steps c) to e) in the opposite direction, i.e. starting from the last slice ($n_2$ or $n_{last}$), wherein after the repetition an average number of connected pores is computed as an average connectivity result.

4. The method according to claim 3 wherein a permeability connectivity index (PCI) is computed which is defined as the average number of connected pores divided by the total number of image pixels.

5. The method according to claim 1 wherein the grid defines squared image pixels.

6. The method according to claim 5 wherein each image pixel has nine neighboring image pixels in the previous and/or the subsequent slice.

7. The method according to claim 1 wherein the porous medium is a rock.

8. System comprising means for carrying out the method according to claim 1.

9. The system according to claim 8 wherein said means comprise an imaging system and a computer.

10. The system according to claim 8 wherein said means comprise an imaging system which is a computed tomography scanner.

* * * * *